(12) United States Patent
Ohnishi et al.

(10) Patent No.: US 10,041,954 B2
(45) Date of Patent: Aug. 7, 2018

(54) BIOMARKER FOR PSYCHIATRIC AND NEUROLOGICAL DISORDERS

(71) Applicant: RESVO Inc., Ota-ku (JP)

(72) Inventors: Arata Ohnishi, Chiba (JP); Takafumi Minamimoto, Chiba (JP); Tetsuya Suhara, Chiba (JP)

(73) Assignee: RESVO INC., Ota-Ku, Tokyo (JP)

( * ) Notice: Subject to any disclaimer, the term of this patent is extended or adjusted under 35 U.S.C. 154(b) by 20 days.

(21) Appl. No.: 14/891,301

(22) PCT Filed: Mar. 18, 2014

(86) PCT No.: PCT/JP2014/057227
§ 371 (c)(1),
(2) Date: Nov. 13, 2015

(87) PCT Pub. No.: WO2014/185145
PCT Pub. Date: Nov. 20, 2014

(65) Prior Publication Data
US 2016/0131663 A1    May 12, 2016

(30) Foreign Application Priority Data
May 16, 2013  (JP) ................ 2013-104124

(51) Int. Cl.
*G01N 33/53*      (2006.01)
*G01N 33/567*     (2006.01)
*G01N 33/68*      (2006.01)
*C07K 16/42*      (2006.01)

(52) U.S. Cl.
CPC ......... *G01N 33/6857* (2013.01); *C07K 16/42* (2013.01); *G01N 33/6863* (2013.01); *G01N 33/6869* (2013.01); *G01N 33/6893* (2013.01); *G01N 33/6896* (2013.01); *G01N 2333/525* (2013.01); *G01N 2333/545* (2013.01); *G01N 2333/5412* (2013.01); *G01N 2800/2821* (2013.01); *G01N 2800/301* (2013.01); *G01N 2800/302* (2013.01); *G01N 2800/304* (2013.01)

(58) Field of Classification Search
None
See application file for complete search history.

(56) References Cited

U.S. PATENT DOCUMENTS

| 5,876,961 A * | 3/1999 | Crowe | C07K 16/00 435/252.3 |
|---|---|---|---|
| 2012/0238936 A1 | 9/2012 | Hyde et al. | |
| 2012/0251553 A1 | 10/2012 | Bahn et al. | |

FOREIGN PATENT DOCUMENTS

| JP | 2011-506995 | 3/2011 |
|---|---|---|
| JP | 2012-013415 | 2/2012 |
| WO | WO 1993/02190 | 2/1993 |
| WO | WO 2004/039956 A2 | 5/2004 |
| WO | WO 2006/089294 A2 | 8/2006 |
| WO | WO 2007/094472 A1 | 8/2007 |
| WO | WO 2010/141716 A2 | 12/2010 |
| WO | WO 2011/144934 A1 | 11/2011 |
| WO | WO 2012/078623 A2 | 6/2012 |
| WO | WO-2009/077763 | 6/2013 |
| WO | WO 2014/185145 A1 | 11/2014 |

OTHER PUBLICATIONS

Bradwell, A.R., Serum Free Light Chain Analysis (plus Hevylite) 2010, 6$^{th}$ Edition, Section 2, 61 pages.
Bradwell, A.R., Serum Free Light Chain Analysis (plus Hevylite) 2010, 6$^{th}$ Edition, Sections 3-6, 64 pages.
International Search Report in PCT/JP2014/057227, dated Jun. 24, 2014, 2 pages.
Fagnart et al., Free kappa and lambda light chain levels in the cerebrospinal fluid of patients with multiple sclerosis and other neurological diseases (1988) *Journal of Neuroimmunology* 19:119-132.
Katzmann et al., Serum Reference Intervals and Diagnostic Ranges for Free κ and Free λ Immunoglobulin Light Chains: Relative Sensitivity for Detection of Monoclonal Light Chains (2002) *Clinical Chemistry* 48(9):1437-1444.
Kuku et al., Serum Proinflammatory Mediators at Different Periods of Therapy in Patients With Multiple Myeloma (2005) 2005(3):171-174.
Oh-Nishi et al., Maternal immune activation by polyriboinosinic-polyribocytidilic acid injection produces synaptic dysfunction but not neuronal loss in the hippocampus of juvenile rat offspring (2010) *Brain Research* 1363:170-179.
Popović et al., Light chain deposition disease restricted to the brain: the first case report (2007) *Human Pathology* 38:179-184.
Rao et al., Serum immunoglobulins and schizophrenia (1985) *Indian Journal of Psychiatry* 27(4):325-328.
Shi et al., Maternal Influenza Infection Causes Marked Behavioral and Pharmacological Changes in the Offspring (2003) *The Journal of Neuroscience* 23(1):297-302.

(Continued)

Primary Examiner — Olga N Chernyshev
(74) Attorney, Agent, or Firm — Squire Patton Boggs (US) LLP

(57) ABSTRACT

The purpose of the present invention is to provide: a biomarker for psychiatric and neurological disorders, in particular, a biomarker for diagnosing psychiatric and neurological disorders; and a test kit and test method for psychiatric and neurological disorders. The inventors discovered that there is a significant increase in the concentration of free κ immunoglobulin chains and free λ immunoglobulin chains in the blood samples from patients with psychiatric and neurological disorders. Consequently, the present invention provides a biomarker for psychiatric and neurological disorders that includes at least one selected from the group consisting of free κ immunoglobulin chains, free λ immunoglobulin chains, and fragments thereof. Using this biomarker for psychiatric and neurological disorders enables the psychiatric and neurological disorders to be easily tested and diagnosed with the blood samples from the subjects. The biomarker enables more effective tests and diagnoses to be conducted combining inflammatory cytokines in the blood of patients with psychiatric and neurological disorders.

10 Claims, 2 Drawing Sheets

(56) References Cited

OTHER PUBLICATIONS

Tsirakis et al., Assessment of proliferating cell nuclear antigen and its relationship with proinflammatory cytokines and parameters of disease activity in multiple myeloma patients (2011) *European Journal of Histochemistry* 55:(e21)113-116.

Popovic et al., "Light chain deposition disease restricted to the brain: the first case report", *Human Pathology*, Saunders, Philadelphia, PA, US, Dec. 12, 2006, vol. 38, No. 1, pp. 179-184, XP005820477.

Brebner et al., "Polyclonal free light chains: a biomarker of inflammatory disease or treatment target?" *F1000 medicine reports*, Jan. 1, 2013, p. 4, XP055346393 (doi 10.3410/M5-4), England.

Hutchison et al., "Polyclonal Immunoglobulin Free Light Chains as a PotentialBiomarker of Immune Stimulation and Inflammation", *Clinical Chemistry*, Oct. 1, 2011, vol. 57, No. 10, pp. 1387-1389, XP055346581, Washington, DC.

Fagnart et al., "Free kappa and lambda light chain levels in the cerebrospinal fluid of patients with multiple sclerosis and other neurological diseases", *Journal of Neuroimmunology*, Elsevier Science Publishers BV, NL, Aug. 1, 1988, vol. 19, No. 1-2, pp. 119-132, XP023694532.

Richard et al., "Schizophrenia and the immune system: Pathophysiology, prevention, and treatment", *American Journal of Health-System Pharmacy*, May 1, 2012, vol. 69, No. 9, pp. 757-766, XP055346122.

Ronco et al., "Immunoglobulin Light (Heavy)-Chain Deposition Disease: From Molecular Medicine to Pathophysiology-Driven Therapy", *Clinical Journal of the American Society of Nephrology*, Oct. 11, 2006, vol. 1, No. 6, pp. 1342-1350, XP055346359.

Supplementary Partial European Search Report dated Mar. 2, 2017 in the European Patent Application No. EP14797879.5, 10 pages.

Office Action dated Apr. 18, 2017 in the Japanese Patent Application No. 2013-104124 with English translation, 5 pages.

"Freelite(TM) Human Lambda Free Kit for use on the Olympus AU(TM) series for in-vitro diagnostic use Product Code: LK018. AU", The Binding Site Group Ltd., PO Box 11712, Birmingham B14 4ZB, UK, Nov. 16, 2009 (Nov. 16, 2009), pp. 1-3, XP055389388.

"Freelite(TM) Human Kappa Free kit for use on the Roche cobas c systems for in-vitro diagnostic use Product Code: LK016.CB", The Binding Site Group Ltd., PO Box 11712, Birmingham B14 4ZB, UK, Oct. 22, 2009 (Oct. 22, 2009), pp. 1-2, XP055389391.

Supplementary Extended European Search Report dated Jul. 21, 2017 in the European Patent Application No. EP14797879.5, 18 pages (2017).

* cited by examiner

[Fig. 1]
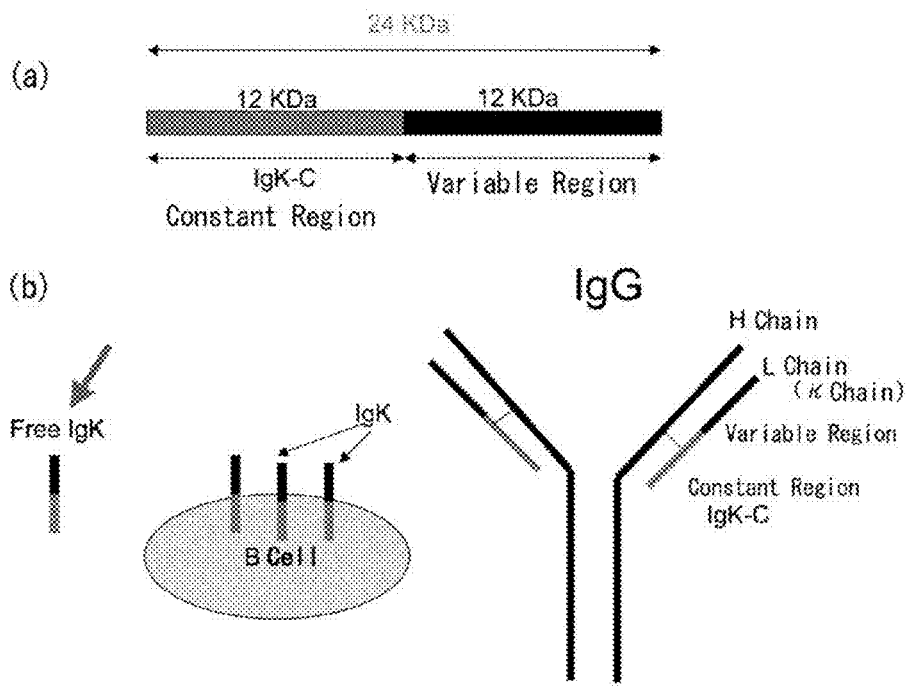
[Fig. 2]
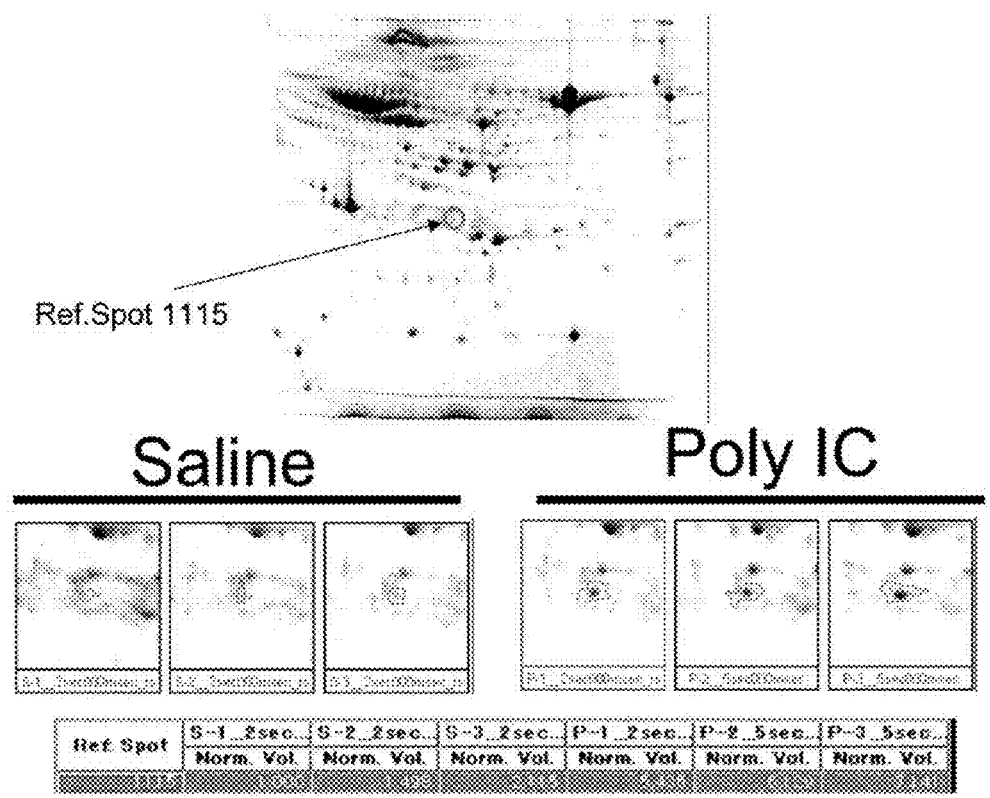

[Fig. 3]
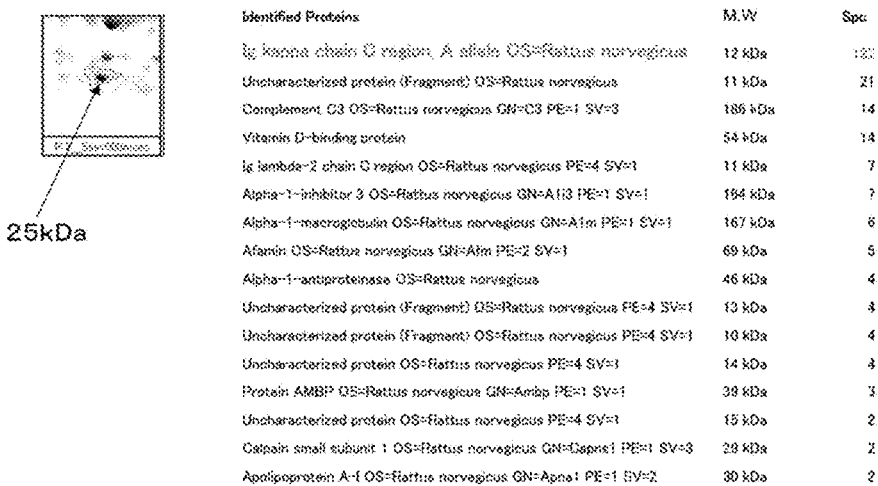
[Fig. 4]
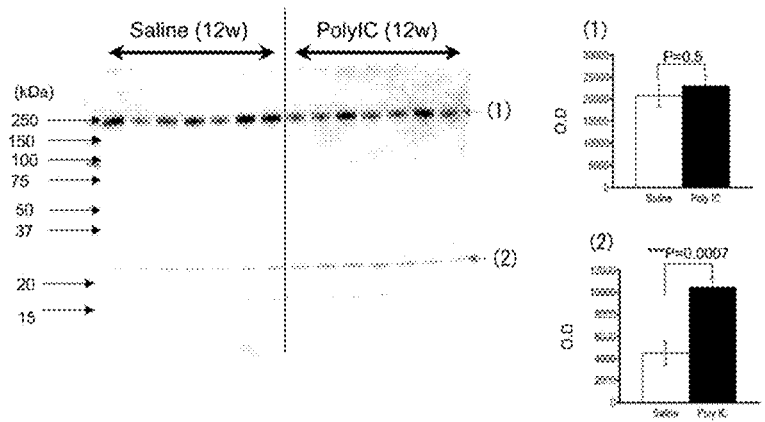
[Fig. 5]
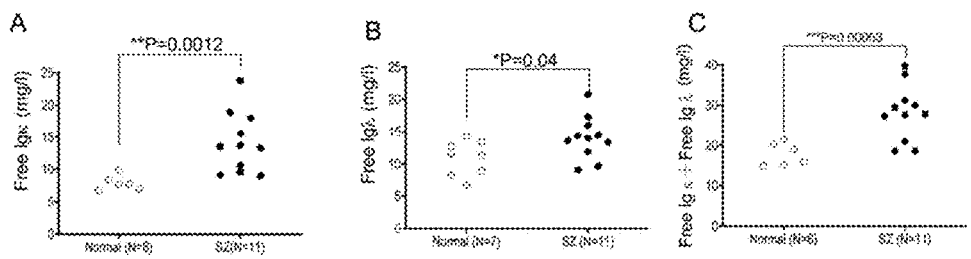

BIOMARKER FOR PSYCHIATRIC AND NEUROLOGICAL DISORDERS

TECHNICAL FIELD

The present invention relates to a biomarker for a psychiatric/neurological disorder, particularly a biomarker for diagnosing a psychiatric/neurological disorder. The present invention also relates to a test kit for a psychiatric/neurological disorder for detecting the biomarker, and a test method for a psychiatric/neurological disorder using the biomarker.

BACKGROUND ART

Diagnosis criteria, such as DMSIV-TR, ICD-10, and PANSS, are currently used as indications in diagnosing psychiatric/neurological disorders, such as schizophrenia, autism, and Alzheimer's disease. However, diagnoses using these criteria are performed by, for example, a medical examination by interview with patients and thus have had the problem of producing variations depending on the evaluator. Thus, there has been a need for a biomarker as an objective biological indication.

Attempts have also been previously made to search for biomarkers for diagnosing psychiatric/neurological disorders. For example, Patent Literature 1 discloses a schizophrenia marker. Patent Literature 2 discloses a biomarker for diagnosing and monitoring mental disorder. However, these markers are not put to practical use in view of accuracy, easiness to practice, cost, and the like.

CITATION LIST

Patent Literature

Patent Literature 1: Japanese Patent Laid-Open No. 2012-013415
Patent Literature 2: Japanese Translation of PCT Application No. 2011-506995

Non-Patent Literature

Non-patent Literature 1: Serum reference intervals and diagnostic ranges for free kappa and free lambda immunoglobulin light chains: relative sensitivity for detection of monoclonal light chains. Katzmann J A, Clark R J, Abraham R S, Bryant S, Lymp J F, Bradwell A R, Kyle R A. Clin Chem. 2002 September; 48(9): 1437-44.
Non-patent Literature 2: Assessment of proliferating cell nuclear antigen and its relationship with proinflammatory cytokines and parameters of disease activity in multiple myeloma patients. Tsirakis G, Pappa C A, Kaparou M, Katsomitrou V, Hatzivasili A, Alegakis T, Xekalou A, Stathopoulos E N, Alexandrakis M G. Eur J Histochem. 2011; 55(3): e21.
Non-patent Literature 3: Serum proinflammatory mediators at different periods of therapy in patients with multiple myeloma. Kuku I, Bayraktar M R, Kaya E, Erkurt M A, Bayraktar N, Cikim K, Aydogdu I. Mediators Inflamm 2005 Aug. 14; 2005(3): 171-4.

SUMMARY OF INVENTION

Technical Problem

An object of the present invention is to provide a biomarker for a psychiatric/neurological disorder, particularly a biomarker for diagnosing a psychiatric/neurological disorder, a test kit for a psychiatric/neurological disorder for detecting the biomarker, and a test method using the biomarker.

Solution to Problem

In view of the above-described problems, the present inventors conducted studies for identifying a biomarker for a psychiatric/neurological disorder. As a result, the present inventors have discovered that the blood concentration of the free κ immunoglobulin chain (containing the constant region) and the free λ immunoglobulin chain (containing the constant region) is significantly increased in patients with psychiatric/neurological disorders compared to that in healthy individuals. Thus, the present invention provides a biomarker for a psychiatric/neurological disorder, comprising at least one selected from the group consisting of the free κ immunoglobulin chain, the free λ immunoglobulin chain, and fragments thereof. The biomarker can be used to readily conduct the test, diagnosis, and the like of a psychiatric/neurological disorder with a blood sample of interest.

In one embodiment, the free κ immunoglobulin chain comprises the amino acid sequence of SEQ ID NO: 1 (constant region) and the free λ immunoglobulin chain comprises the amino acid sequence of SEQ ID NO: 6 (constant region). In one embodiment, the free κ immunoglobulin chain comprises the amino acid sequence of SEQ ID NO: 2 or 3 and the free λ immunoglobulin chain comprises the amino acid sequence of SEQ ID NO: 6.

It is known that the free κ immunoglobulin chain increases also in the serum of patients having multiple myeloma (Non-patent Literature 1). It is known that in this case, an inflammatory cytokine increases simultaneously (Non-patent Literatures 2 and 3). The present inventors have surprisingly discovered that in patients with psychiatric/neurological disorders, the inflammatory cytokine does not increase despite an increase in the free κ immunoglobulin chain. Thus, the present invention provides a biomarker for a psychiatric/neurological disorder, comprising an inflammatory cytokine in addition to the above biomarker. In one embodiment, the inflammatory cytokine is at least one selected from the group consisting of IL-6, IL-1 beta, and TNF-alpha.

The present invention also provides a test kit for a psychiatric/neurological disorder, comprising a substance capable of detecting the biomarker for a psychiatric/neurological disorder. In addition, the present invention provides a test method for a psychiatric/neurological disorder, using the biomarker as an indication. In one embodiment, the test method for a psychiatric/neurological disorder according to the present invention comprises the steps of (a) measuring the amount of the biomarker for a psychiatric/neurological disorder according to the present invention in a blood sample from a subject and (b) comparing the amount with that from a normal subject or with the median value of that from a normal subject.

Advantageous Effects of Invention

The biomarker for a psychiatric/neurological disorder according to the present invention can be easily collected and quantified from a blood sample from a subject, and thus the use of the biomarker for a psychiatric/neurological disorder according to the present invention enables the rapid and simple diagnosis and the like of a psychiatric and neurological disorder.

BRIEF DESCRIPTION OF DRAWINGS

FIG. 1 is a diagram explaining a κ immunoglobulin chain. FIG. 1(a) shows the construction and approximate molecular weight of the κ immunoglobulin chain. FIG. 1(b) shows the expression place and location of the κ immunoglobulin chain. The κ immunoglobulin chain (Ig κ) consists of a constant region of about 12 kDa called a κ immunoglobulin chain C region (Ig κ-C) and a variable region of about 12 kDa (FIG. 1 (a)), and one in free form and one expressed in IgG (also including IgA and IgM) or on B cells are identified (FIG. 1(b)).

FIG. 2 shows the results of separating serum proteins obtained from a group of maternal immune activation model rats prepared by administering Poly IC to their mother bodies (schizophrenia and autism model animals) (MIA rats) (denoted by "Poly IC" in the figure) and a group of control rats prepared by administering saline to their mother bodies (denoted by "Saline" in the figure), by a 2-dimensional electrophoresis method. A difference was observed in a spot of about 25 kDa (Ref. Spot 1115).

FIG. 3 shows the results of the LC MS/MS measurement of the spot (Ref. Spot 1115, molecular weight: about 25 kDa) in which a difference was observed in the 2-dimensional electrophoresis gel image shown in FIG. 2. These results showed that a concordant difference existed in the level of Ig κ-C expression in sera between 3 individuals in the MIA rat group and 3 individuals in the control rat group.

FIG. 4 shows the results of denaturing sera from the MIA rat group (denoted by "Poly IC" in the figure) and the control rat group (denoted by "Saline" in the figure) with SDS alone (100° C., 5 minutes), followed by Western blotting with an anti-Ig κ-C antibody. A significant difference was observed in a band of about 25 kDa ((2) in the figure) between the MIA rats and the control rats. The band was probably a free κ immunoglobulin chain since it was detected without the cleavage of S-S bonds or hydrogen bonds.

FIG. 5 shows the results of comparing the concentrations (mg/l) of a free κ immunoglobulin chain (A in the figure) and a free λ immunoglobulin chain (B in the figure) in sera from a group of schizophrenia patients (SZ) and a normal group. The concentrations of the free κ immunoglobulin chain (containing a constant region) and the free λ immunoglobulin chain (containing a constant region) significantly increased in schizophrenia patients (SZ). As a result of comparing the concentration of the free κ immunoglobulin chain+the free λ immunoglobulin chain (C in the figure), a further significant difference was observed (P=0.00063).

DESCRIPTION OF EMBODIMENTS (1. Definition)

As used herein, the term "psychiatric/neurological disorder" has the meaning generally used in the art, and examples thereof include schizophrenia, autism, Alzheimer's disease, cognitive abnormality, bipolar disorder (manic-depressive psychosis), disorders of cranial nerve development, cognitive impairment ascribed to neuropathy due to infection during pregnancy, mental disorder ascribed to impaired immunity, epilepsy, idiophrenic mental disorder, toxic mental disorder, intellectual disability (mental retardation), psychopathy, and neurosis. In addition, the "psychiatric/neurological disorder" also includes syphilitic mental disorder, senile mental disorder, cerebrovascular mental disorder, mental disorder due to head injury, atypical endogenous psychosis, endocrine mental disorder and exogenous reaction type, and involutional mental disorder. In the present invention, the psychiatric/neurological disorder is preferably schizophrenia, autism, or Alzheimer's disease, most preferably schizophrenia.

As used herein, the term "biomarker for a psychiatric/neurological disorder" refers to a living substance capable of being an indication for determining whether the psychiatric/neurological disorder have been developed or can be potentially developed, or determining prognosis after developing the disorders. For example, the biomarker for a psychiatric/neurological disorder can be used to diagnose the psychiatric/neurological disorder by measuring its amount. The biomarker for a psychiatric/neurological disorder may comprise a plurality of biomarkers. For example, when 2 or more living substances change in quantity in a subject with a psychiatric/neurological disorder, a combination of the 2 or more living substances can be a biomarker for the psychiatric/neurological disorder. For example, when certain 2 living substances simultaneously increase in a subject with another disorder or condition other than a psychiatric/neurological disorder but one of them increases while the other not increasing in a subject with the psychiatric/neurological disorder, a combination of the 2 living substances can also be a biomarker for the psychiatric/neurological disorder. The biomarker for a psychiatric/neurological disorder can be used, by measuring its amount, for the diagnosis and test of the psychiatric/neurological disorder, the screening of subjects having the psychiatric/neurological disorder, the establishment of an efficient therapeutic method, the screening of a candidate agent useful for the psychiatric/neurological disorder, and the development of model animals for the psychiatric/neurological disorder.

The term "κ immunoglobulin chain" and the term "λ immunoglobulin chain" mean the 2 types (κ type and λ type) of an immunoglobulin L chain, respectively. They are herein also referred to as "Ig κ" and "Ig λ", respectively. The κ immunoglobulin chain (Ig κ) is a polypeptide consisting of a constant region of about 12 kDa called a κ immunoglobulin chain C region (Ig κ-C) and a variable region of about 12 kDa (see (a) in FIG. 1), and one in free form and one expressed in IgG or on B cells are known (see (b) in FIG. 1). The λ immunoglobulin chain (Ig λ) is an isoform of the κ immunoglobulin chain (Ig κ), and consists of a constant region and a variable region as is the case with the κ immunoglobulin chain (Ig κ).

The term "κ immunoglobulin chain C region" is a polypeptide forming the constant region of a κ immunoglobulin chain or a free κ immunoglobulin chain. The polypeptide is herein also referred to as "Ig κ chain C" or "Ig κ-C". As used herein, the "λ immunoglobulin chain C region" is a polypeptide forming the constant region of a λ immunoglobulin chain or a free λ immunoglobulin chain. The polypeptide is also referred to as "Ig λ chain C" or "Ig λ-C".

As used herein, the term "free κ immunoglobulin chain" and the term "free λ immunoglobulin chain" mean a κ immunoglobulin chain in free form and a λ immunoglobulin chain in free form, respectively (see (b) in FIG. 1). The term "free" means being present alone without expression in IgG or on B cells or the like. The free κ immunoglobulin chain contains the κ immunoglobulin chain C region. The free κ immunoglobulin chain is herein also referred to as "free Ig κ". The free λ immunoglobulin chain is also referred to as "free Ig λ". The free λ immunoglobulin chain contains the λ immunoglobulin chain C region.

In the context of the biomarker for a psychiatric/neurological disorder according to the present invention herein, "fragment" refers to a polypeptide containing a partial amino acid sequence of a full-length protein (or a polypeptide). Thus, the "fragment" is a polypeptide which has a length within the full length of the biomarker for a psychiatric/neurological disorder according to the present invention and is at least one amino acid residue shorter, for example, 1 to 100, 1 to 50, 1 to 20, 19, 18, 17, 16, 15, 14, 13, 12, 11, 10, 9, 8, 7, 6, 5, 4, 3, 2, or 1 amino acid residue shorter, than the full length. Preferably, the fragment of the free κ immunoglobulin chain is the κ immunoglobulin chain C region or a site capable of being an antigen in detection with an antibody. Preferably, the fragment of the free λ immunoglobulin chain is the λ immunoglobulin chain C region or a site capable of being an antigen in detection with an antibody.

As used herein, the term "measurement" includes detection and quantification. The term "quantification" also includes semi-quantification. As used herein, the term "blood sample" refers to blood collected from a subject, and includes serum, plasma, and whole blood.

As used herein, the term "subject" means any mammal, for example, humans, rats, mice, guinea pigs, rabbits, monkeys (for example, marmosets, particularly common marmosets, or rhesus monkeys), dogs, cats, or miniature pigs. The subject is preferably a human. As used herein, the term "normal subject" means a subject not having developed or potentially not developing a psychiatric/neurological disorder, for example, a human, a rat, a mouse, a guinea pig, a rabbit, a monkey (for example, marmosets, particularly common marmosets, or rhesus monkeys), a dog, a cat, or a miniature pig not having developed or potentially not developing a psychiatric/neurological disorder. The normal subject is preferably a human. The "normal subject" and "normal control" can be herein synonymously used. When the normal subject is a human, the normal subject is herein also referred to as a healthy individual.

(2. Biomarker for Psychiatric/Neurological Disorder According to Present Invention)

The biomarker for a psychiatric/neurological disorder according to the present invention comprises at least one selected from the group consisting of a free κ immunoglobulin chain, a free λ immunoglobulin chain, and fragments thereof. Preferably, the biomarker for a psychiatric/neurological disorder according to the present invention consists of at least one selected from the group consisting of a free κ immunoglobulin chain, a free λ immunoglobulin chain, and fragments thereof. More preferably, the biomarker for a psychiatric/neurological disorder according to the present invention comprises a free κ immunoglobulin chain or a fragment thereof. Alternatively, more preferably, the biomarker for a psychiatric/neurological disorder according to the present invention consists of a free κ immunoglobulin chain or a fragment thereof. More preferably, the biomarker for a psychiatric/neurological disorder according to the present invention comprises a free λ immunoglobulin chain or a fragment thereof. Alternatively, more preferably, the biomarker for a psychiatric/neurological disorder according to the present invention consists of a free λ immunoglobulin chain or a fragment thereof. More preferably, the biomarker for a psychiatric/neurological disorder according to the present invention comprises a free κ immunoglobulin chain or a fragment thereof and a free λ immunoglobulin chain or a fragment thereof. Alternatively, more preferably, the biomarker for a psychiatric/neurological disorder according to the present invention consists of a free κ immunoglobulin chain or a fragment thereof and a free λ immunoglobulin chain or a fragment thereof.

In another embodiment, the biomarker for a psychiatric/neurological disorder according to the present invention comprises at least one selected from the group consisting of a free κ immunoglobulin chain, a free λ immunoglobulin chain, and fragments thereof, and an inflammatory cytokine. Preferably, the biomarker for a psychiatric/neurological disorder according to the present invention consists of at least one selected from the group consisting of a free κ immunoglobulin chain, a free λ immunoglobulin chain, and fragments thereof, and an inflammatory cytokine. More preferably, the biomarker for a psychiatric/neurological disorder according to the present invention comprises a free κ immunoglobulin chain or a fragment thereof, and an inflammatory cytokine. Alternatively, more preferably, the biomarker for a psychiatric/neurological disorder according to the present invention consists of a free κ immunoglobulin chain or a fragment thereof, and an inflammatory cytokine. More preferably, the biomarker for a psychiatric/neurological disorder according to the present invention comprises a free λ immunoglobulin chain or a fragment thereof, and an inflammatory cytokine. Alternatively, more preferably, the biomarker for a psychiatric/neurological disorder according to the present invention consists of a free λ immunoglobulin chain or a fragment thereof, and an inflammatory cytokine. More preferably, the biomarker for a psychiatric/neurological disorder according to the present invention comprises a free κ immunoglobulin chain or a fragment thereof, a free λ immunoglobulin chain or a fragment thereof, and an inflammatory cytokine. Alternatively, more preferably, the biomarker for a psychiatric/neurological disorder according to the present invention consists of a free κ immunoglobulin chain or a fragment thereof, a free λ immunoglobulin chain or a fragment thereof, and an inflammatory cytokine.

In one embodiment, the inflammatory cytokine is at least one selected from the group consisting of IL-6, IL-1 beta, and TNF-alpha. Preferably, the inflammatory cytokine is at least two selected from the group consisting of IL-6, IL-1 beta, and TNF-alpha. More preferably, the inflammatory cytokine is IL-6, IL-1 beta, and TNF-alpha. In one embodiment, the biomarker for a psychiatric/neurological disorder according to the present invention is present in a blood sample collected from a subject.

The amino acid sequence of a free κ immunoglobulin chain is well-known to those of ordinary skill in the art. The human-derived free κ immunoglobulin chain comprises a constant region (κ immunoglobulin chain C region). For example, the free κ immunoglobulin chain comprises the amino acid sequence of SEQ ID NO: 1 (C region). Preferably, the free κ immunoglobulin chain comprises the amino acid sequence of SEQ ID NO: 2 or 3. Those of ordinary skill in the art can detect and quantify the free κ immunoglobulin chain using a substance capable of recognizing the constant region (κ immunoglobulin chain C region) or an antigen site thereof. Examples of the substance include Anti-Ig κ light chain antibody (MAR-C8) (Abcam Co., Ltd.) and FREELITE κ chain (MBL Co., Ltd., code number: BS-LK016BD).

The constant region (κ immunoglobulin chain C region) preferably comprises the amino acid sequence of SEQ ID NO: 1. Alternatively, the constant region (κ immunoglobulin chain C region) preferably consists of the amino acid sequence of SEQ ID NO: 1. More preferably, the constant region (κ immunoglobulin chain C region) comprises the amino acid sequence of SEQ ID NO: 2 or 3. The antigen site of the constant region (κ immunoglobulin chain C region) preferably comprises the amino acid sequence of SEQ ID NO: 2 or 3. Alternatively, the antigen site of the constant region (κ immunoglobulin chain C region) preferably consists of the amino acid sequence of SEQ ID NO: 2 or 3. The fragment of the free κ immunoglobulin chain preferably comprises the constant region (κ immunoglobulin chain C region) or an antigen site thereof. Alternatively, the fragment of the free κ immunoglobulin chain preferably consists of the constant region (κ immunoglobulin chain C region) or an antigen site thereof.

A free κ immunoglobulin chain comprising the amino acid sequence of SEQ ID NO: 4 (rat-derived) or SEQ ID NO: 5 (rat-derived) can be used to test, diagnose, and/or determine whether psychiatric/neurological disorder model animals (particularly, rats) have developed or can potentially develop the psychiatric/neurological disorder. It is useful, particularly for the preparation, quality control, or the like of psychiatric/neurological disorder model animals. The test method can be similarly performed by the method shown in the section "Test Method for Psychiatric/Neurological Disorder" below. Thus, in another embodiment, the free κ immunoglobulin chain comprises the amino acid sequence of SEQ ID NO: 4 (C region). Preferably, the free κ immunoglobulin chain comprises the amino acid sequence of SEQ ID NO: 5. The constant region (κ immunoglobulin chain C region) preferably comprises the amino acid sequence of SEQ ID NO: 4. Alternatively, the constant region (κ immunoglobulin chain C region) preferably consists of the amino acid sequence of SEQ ID NO: 4. The antigen site of the constant region (κ immunoglobulin chain C region) preferably comprises the amino acid sequence of SEQ ID NO: 5. Alternatively, the antigen site of the constant region (κ immunoglobulin chain C region) preferably consists of the amino acid sequence of SEQ ID NO: 5. The fragment of the free κ immunoglobulin chain preferably comprises the constant region (κ immunoglobulin chain C region) or an antigen site thereof. Alternatively, the fragment of the free κ immunoglobulin chain preferably consists of the constant region (κ immunoglobulin chain C region) or an antigen site thereof.

The amino acid sequence of a free λ immunoglobulin chain is also well-known to those of ordinary skill in the art. The free λ immunoglobulin chain comprises a constant region (λ immunoglobulin chain C region). For example, the free λ immunoglobulin chain comprises the amino acid sequence of SEQ ID NO: 6. Preferably, the free λ immunoglobulin chain comprises the antigen site of the constant region (λ immunoglobulin chain C region). Those of ordinary skill in the art can readily detect and quantify the free λ immunoglobulin chain using a substance capable of recognizing the constant region (λ immunoglobulin chain C region) or an antigen site thereof. Examples of the substance include Anti-Ig λ light chain (human) pAb-FITC (MBL Co., Ltd.) and FREELITE λ chain (MBL Co., Ltd., code number: BS-LK018BD).

The constant region (λ immunoglobulin chain C region) preferably comprises the amino acid sequence of SEQ ID NO: 6. Alternatively, the constant region (λ immunoglobulin chain C region) preferably consists of the amino acid sequence of SEQ ID NO: 6. The fragment of the free λ immunoglobulin chain preferably comprises the λ immunoglobulin chain C region or an antigen site thereof. Alternatively, the fragment of the free λ immunoglobulin chain preferably consists of the λ immunoglobulin chain C region or an antigen site thereof.

The relation between SEQ ID NO and the κ immunoglobulin chain C region or the λ immunoglobulin chain C region is as follows.

SEQ ID NO: 1—κ immunoglobulin chain C region (human-derived)
SEQ ID NO: 2—antigen site (human-derived)
SEQ ID NO: 3—antigen site (human-derived)
SEQ ID NO: 4—κ immunoglobulin chain C region (rat-derived)
SEQ ID NO: 5—antigen site (rat-derived)
SEQ ID NO: 6—λ immunoglobulin chain C region (human-derived)

The free κ immunoglobulin chain is a polypeptide consisting of a constant region (λ immunoglobulin chain C region) of about 12 kDa and a variable region of about 12 kDa (see FIG. 1($a$)). Thus, the measurement of the polypeptide amount of the κ immunoglobulin chain C region will mean to measure the amount of the free κ immunoglobulin chain. Similarly, the measurement of the polypeptide amount of the λ immunoglobulin chain C region will mean to measure the amount of the free λ immunoglobulin chain.

In another embodiment, the biomarker for a psychiatric/neurological disorder according to the present invention comprises a polypeptide containing the antigen site of a free κ immunoglobulin chain, or a fragment thereof. Alternatively, the biomarker for a psychiatric/neurological disorder according to the present invention consists of a polypeptide containing the antigen site of a free κ immunoglobulin chain, or a fragment thereof. In still another embodiment, the biomarker for a psychiatric/neurological disorder according to the present invention comprises a polypeptide containing a free κ immunoglobulin chain C region, or a fragment thereof. Alternatively, the biomarker for a psychiatric/neurological disorder according to the present invention consists of a polypeptide containing a free κ immunoglobulin chain C region, or a fragment thereof. In another embodiment, the biomarker for a psychiatric/neurological disorder according to the present invention comprises a polypeptide containing the antigen site of a free λ immunoglobulin chain, or a fragment thereof. Alternatively, the biomarker for a psychiatric/neurological disorder according to the present invention consists of a polypeptide containing the antigen site of a free λ immunoglobulin chain, or a fragment thereof. In still another embodiment, the biomarker for a psychiatric/neurological disorder according to the present invention comprises a polypeptide containing a free λ immunoglobulin chain C region, or a fragment thereof. Alternatively, the biomarker for a psychiatric/neurological disorder according to the present invention consists of a polypeptide containing a free λ immunoglobulin chain C region, or a fragment thereof.

Those of ordinary skill in the art will understand that deletion, addition, variation, or substitution in the amino acid sequence of each of the polypeptides having the above amino acid sequences can be permitted provided that the uniqueness of the polypeptide, i.e., a specific amino acid sequence characterizing the polypeptide (e.g., a motif, a domain, a box sequence, or the like), or the like, is retained. The number of such deletions, additions, variations, or substitutions is not limited (for example, 1, 2, 3, 4, 5, 6, 7, 8, 9, 10, or more) provided that the uniqueness of the biomarker for a psychiatric/neurological disorder according to the present invention is retained. In general, variation or substitution between amino acids having the same properties has no or little effect on the function of the polypeptide; thus, a polypeptide containing the variation or substitution can be equated with the original polypeptide (for example, a polypeptide specified by any of the above SEQ ID NOS). The properties of such amino acids can be categorized, for example, as follows: acidic amino acids (aspartic acid and glutamic acid), basic amino acids (lysine, histidine, and arginine), hydrophobic (aliphatic) amino acids (glycine, alanine, valine, leucine, and isoleucine), sulfur-containing amino acids (methionine and cysteine), aromatic amino acids (phenylalanine, tryptophan, and tyrosine), acidic amino acid amides (asparagine and glutamine), or neutral amino acids (glycine, alanine, valine, leucine, isoleucine, phenylalanine, tyrosine, tryptophan, proline, serine, threonine, cysteine, methionine, asparagine, and glutamine).

For example, an amino acid sequence in which Glu at the 105th position and Cys at the 106th position are deleted in the amino acid sequence of SEQ ID NO: 1 is also included within the scope of the present invention.

Those of ordinary skill in the art will understand that the biomarker for a psychiatric/neurological disorder according to the present invention can also include one modified, for example, with phosphorylation, sugar chain addition, amidation, ubiquitination, or acetylation.

The biomarker for a psychiatric/neurological disorder according to the present invention can be present in a blood, urine, or spinal fluid sample from a subject. The sample is preferably a blood sample (serum, plasma, or whole blood). The blood sample is more preferably serum. The collection of a blood sample from a subject can be performed by a common method well-known to those of ordinary skill in the art. The blood sample can be collected, for example, using a syringe.

All of a free κ immunoglobulin chain, a free λ immunoglobulin chain, and fragments thereof in the blood sample of the subject increase significantly. Thus, their change can be measured to determine the subject as having developed or capable of potentially developing the psychiatric/neurological disorder.

The free κ immunoglobulin chain may also increase, for example, in patients with multiple myeloma. However, it is known that an inflammatory cytokine increases simultaneously in this case (Non-patent Literatures 1 to 3). On the other hand, the present inventors have found that in a subject with psychiatric/neurological disorder, the free κ immunoglobulin chain increases while an increase in an inflammatory cytokine is not observed. Thus, a psychiatric/neurological disorder can be more clearly determined by the combination of the free κ immunoglobulin chain and the inflammatory cytokine, i.e., by using the amount of the free κ immunoglobulin chain or a fragment thereof and the amount of the inflammatory cytokine as indications. The amount of the free λ immunoglobulin chain or a fragment thereof and the amount of the inflammatory cytokine may also be used as indications. Most preferably, the three of the free κ immunoglobulin chain or a fragment thereof, the free λ immunoglobulin chain or a fragment thereof, and the inflammatory cytokine are used as indications.

The biomarker for a psychiatric/neurological disorder according to the present invention is preferably a biomarker for schizophrenia, autism, disorders of cranial nerve development, cognitive impairment ascribed to neuropathy due to infection during pregnancy, or mental disorder ascribed to impaired immunity. Most preferably it is a biomarker for schizophrenia.

The details of the determination of the development or potential development of a psychiatric/neurological disorder will be described in "Test Method for Psychiatric/Neurological Disorder" below.

(3. Test Kit for Psychiatric/Neurological Disorder)

The present invention provides a test kit for a psychiatric/neurological disorder. The test kit can be used to measure the amount of the biomarker for a psychiatric/neurological disorder according to the present invention in a blood sample from a subject to determine whether the subject has developed or is at risk of developing the psychiatric/neurological disorder.

The test kit of the present invention contains a substance capable of detecting the biomarker for a psychiatric/neurological disorder according to the present invention. When the biomarker for a psychiatric/neurological disorder comprises a plurality of biomarkers, the kit can contain a plurality of substances capable of detecting the plurality of biomarkers respectively. The substance is not particularly limited; however, it can be any molecule having affinity to the biomarker for a psychiatric/neurological disorder according to the present invention. The substance can be a substance capable of detecting a free κ immunoglobulin chain C region or an antigen site thereof. The substance can be a substance capable of detecting a free λ immunoglobulin chain C region or an antigen site thereof. The substance includes, for example, an antibody, a low molecular compound, a high molecular compound, a protein, a peptide, and a nucleic acid. The substance is preferably labeled with any marker, such as a dye or fluorescent dye, a radioactive isotope, and an enzyme so that the biomarker for a psychiatric/neurological disorder according to the present invention can be detected. The substance is more preferably an antibody. Preferably, the antibody is an anti-Ig κ antibody, an anti-Ig κ-C antibody, an anti-Ig λ antibody, or an anti-Ig λ-C antibody. The antibody may be a monoclonal antibody or a polyclonal antibody.

Examples of the substance capable of detecting the biomarker for a psychiatric/neurological disorder according to the present invention include Anti-Ig κ light chain antibody (MAR-C8) (Abcam Co., Ltd.), FREELITE κ chain (MBL Co., Ltd., code number: BS-LK016BD), Anti-Ig λ light chain (human) pAb-FITC (MBL Co., Ltd.), and FREELITE λ chain (MBL Co., Ltd., code number: BS-LK018BD).

The antibody may be prepared by a method well-known to those of ordinary skill in the art. For example, the biomarker for a psychiatric/neurological disorder according to the present invention can be administered to a mammal, such as a rabbit, for immunization to prepare an antibody from its serum. The anti-Ig κ antibody can be prepared by administering the polypeptide of the κ immunoglobulin chain C region or an antigen site thereof to a mammal, such as a rabbit. For example, the anti-Ig κ antibody is prepared by administering a polypeptide comprising the amino acid sequence of any one of SEQ ID NOS: 1 to 5 or a polypeptide consisting of the amino acid sequence of any one of SEQ ID NOS: 1 to 5. The anti-Ig λ antibody can be prepared by administering the polypeptide of the λ immunoglobulin chain C region or an antigen site thereof to a mammal, such as a rabbit. For example, the anti-Ig λ antibody is prepared by administering a polypeptide comprising the amino acid sequence of SEQ ID NO: 6 or a polypeptide consisting of the amino acid sequence of SEQ ID NO: 6. The antibody may be labeled with any marker, such as a dye (e.g., a fluorescent dye), a radioactive isotope, and an enzyme.

The test kit for a psychiatric/neurological disorder according to the present invention may further contain a labeled secondary antibody. The labeling can be performed using any marker, such as a dye (e.g., a fluorescent dye), a radioactive isotope, and an enzyme.

In a particular embodiment, the substance capable of detecting the biomarker for a psychiatric/neurological disorder according to the present invention, for example, an antibody, is immobilized on a solid-phase support. The solid-phase support may be made of any appropriate material, such as a plastic (e.g., polystyrene resin, polycarbonate resin, polyethylene resin, or polypropylene resin) or glass. The solid-phase support may be a substrate of any shape, such as a dish, a well, a strip, or a chip. The substrate surface may be optionally coated and modified.

The test kit for a psychiatric/neurological disorder according to the present invention may contain instructions showing a method for measuring the amount of the biomarker for a psychiatric/neurological disorder according to the present invention.

In addition, the test kit for a psychiatric/neurological disorder according to the present invention may contain, for example, reagents (for example, a buffer solution, a blocking reagent, an enzyme substrate, and a fluorescent reagent) and/or devices or instruments (for example, a container, a reaction device, a fluorescence measuring instrument) used in the test method for a psychiatric/neurological disorder.

The test kit for a psychiatric/neurological disorder according to the present invention is preferably a test kit for schizophrenia, autism, disorders of cranial nerve development, cognitive impairment ascribed to neuropathy due to infection during pregnancy, or mental disorder ascribed to impaired immunity. Most preferably, it is a test kit for schizophrenia.

The test kit for a psychiatric/neurological disorder according to the present invention can be used for determining the development or potential development of a psychiatric/neurological disorder and prognosis after developing the disorder. The details of the determination will be described in the item of "Test Method for Psychiatric/Neurological Disorder" below. The test kit for a psychiatric/neurological disorder according to the present invention can be used for diagnosing a psychiatric/neurological disorder. The test kit for a psychiatric/neurological disorder according to the present invention can be used in a test method for a psychiatric/neurological disorder shown below.

(4. Test Method for Psychiatric/Neurological Disorder)

The present invention provides a test method for a psychiatric/neurological disorder. The test method uses the amount of the biomarker for a psychiatric/neurological disorder according to the present invention in a blood sample from a subject as an indication. The test method of the present invention is useful for determining the development or potential development of a psychiatric/neurological disorder and prognosis after developing the disorder. The test method of the present invention can also be used for diagnosing a psychiatric/neurological disorder. The test method of the present invention can also provide data necessary for the treatment, prevention, diagnosis, differentiation, or prognosis estimation of a psychiatric/neurological disorder. The test method of the present invention can also provide information useful for determining the development or potential development of a psychiatric/neurological disorder and prognosis after developing the disorder. In addition, a treatment method and a treatment regimen for a subject can be decided from the results obtained using the test method of the present invention. Further, a primary screening of a psychiatric/neurological disorder in a medical checkup and the like can be performed using the test method of the present invention. A screening of a psychiatric/neurological disorder can also be carried out in the first contact of patients in psychiatry.

The test method for a psychiatric/neurological disorder according to the present invention is preferably a test method for schizophrenia, autism, disorders of cranial nerve development, cognitive impairment ascribed to neuropathy due to infection during pregnancy, or mental disorder ascribed to impaired immunity. Most preferably, it is a test kit for schizophrenia.

The test method of the present invention can comprise a step of measuring the amount of the biomarker for a psychiatric/neurological disorder according to the present invention in a subject and a step of comparing the measured amount of the biomarker for a psychiatric/neurological disorder according to the present invention with that in a normal subject. The test method of the present invention can comprise the steps of (a) measuring the amount of at least one selected from the group consisting of a free κ immunoglobulin chain, a free λ immunoglobulin chain, and fragments thereof in a blood sample from a subject and (b) comparing the amount with that from a normal subject. Preferably, the test method of the present invention can comprise the steps of (a) measuring the amount of a free κ immunoglobulin chain or a fragment thereof and a free λ immunoglobulin chain or a fragment thereof in a blood sample from a subject and (b) comparing the amount with that from a normal subject. The comparing step comprises a step of comparison with the median value in the normal control group. The amount is preferably an amount by combining, i.e., the total amounts of a free κ immunoglobulin chain or a fragment thereof and a free λ immunoglobulin chain or a fragment thereof in a blood sample from a subject.

In another embodiment, the test method of the present invention can comprise the steps of (a) measuring the amount of at least one selected from the group consisting of a free κ immunoglobulin chain, a free λ immunoglobulin chain, and fragments thereof and the amount of an inflammatory cytokine in a blood sample from a subject and (b) comparing the amount with that from a normal subject. More preferably, the test method of the present invention comprises the steps of (a) measuring the amount of a free κ immunoglobulin chain or a fragment thereof and a free λ immunoglobulin chain or a fragment thereof and the amount of an inflammatory cytokine in a blood sample from a subject and (b) comparing these amounts with those from a normal subject. The comparing step comprises a step of comparison with the median value in the normal control group. The amount is preferably an amount by combining, i.e., the total amounts of a free κ immunoglobulin chain or a fragment thereof and a free λ immunoglobulin chain or a fragment thereof in a blood sample from a subject.

The details of a psychiatric/neurological disorder, a free κ immunoglobulin chain, a free λ immunoglobulin chain, and fragments thereof, and an inflammatory cytokine have been described in the section "Biomarker for Psychiatric/Neurological Disorder According to Present Invention" and will not be again described.

In the step (a) of the test method of the present invention, the measurement includes detection and quantification. The level of the quantification can be a level that enables the determination of the development or potential development of a psychiatric/neurological disorder or the determination of prognosis after developing the disorders. The quantification may be semi-quantification. The measurement of a free κ immunoglobulin chain may be the detection or quantification of a free κ immunoglobulin chain C region and/or an antigen site thereof. The measurement of a free λ immunoglobulin chain may be the detection of a free λ immunoglobulin chain C region and/or an antigen site thereof. The measurement may be the measurement of the amount of mRNA encoding the biomarker for a psychiatric/neurological disorder according to the present invention.

In the step (a) of the test method of the present invention, the measurement of the amount of the biomarker for a psychiatric/neurological disorder according to the present invention can be carried out by a common method well-known to those of ordinary skill in the art. Examples thereof include a one- or two-dimensional electrophoresis method, a Western blotting method, an enzyme linked immunosorbent assay (ELISA), a sandwich ELISA method, an immunoelectrophoresis method, single radial immunodiffusion (SRID), a radioimmunoassay (RIA), an enzyme immunoassay (EIA), a latex immunoassay (LIA), and a fluorescence immunoassay (FIA). The amount of the biomarker for a psychiatric/neurological disorder according to the present invention can also be measured using the detection kit for a psychiatric/neurological disorder according to the present invention. The amount of the biomarker for a psychiatric/neurological disorder according to the present invention can also be measured using, for example, a device (e.g., a radiation counter, an optical measurement device, or a fluorescence intensity measuring device) and an image analysis software which are well-known to those of ordinary skill in the art. The amount of the biomarker for a psychiatric/neurological disorder according to the present invention may be measured once or a plurality of times.

In the step (a) of the test method of the present invention, the amount of the biomarker for a psychiatric/neurological disorder according to the present invention may be a concentration (e.g., mg/l, µg/l, or pg/ml), a radiation intensity, or a fluorescence intensity. The unit of the amount of the biomarker for a psychiatric/neurological disorder according to the present invention will depend on the measurement method. In a certain embodiment, the amount of the biomarker for a psychiatric/neurological disorder according to the present invention may be a relative ratio to that in a normal subject.

The blood sample may be serum, plasma, or whole blood. The blood sample is preferably serum. The method for collecting the blood sample may be a common method, such as collection using a syringe or the like from a subject, and is not particularly limited. The blood sample collected from a subject may be denatured and/or stored by a method well-known to those of ordinary skill in the art.

Before measuring the blood sample, the blood sample collected from a subject can be prepared using a reagent and a means which are well-known to those of ordinary skill in the art. Examples of the reagent include buffers, such as acetic acid-acetate, phosphoric acid-phosphate, citric acid-citrate, or tris(hydroxymethyl)aminomethane (tris); denaturating agents, such as urea and/or thiourea; reducing agents, such as dithiothreitol (DTT); and surfactants, such as sodium lauryl sulfate (SDS). Examples of the means include filtration, ultrafiltration, centrifugation, homogenization, incubation, shaking, and lyophilization.

In the test method of the present invention, when the free κ immunoglobulin chain, the free λ immunoglobulin chain, and fragments thereof in a blood sample from a subject are measured, denaturation (cleavage of S-S bonds) by DTT may not be conducted. Urea and/or thiourea may also not be used. For example, the blood sample may be denatured only with SDS. The reason therefor is to eliminate the κ immunoglobulin chain and the λ immunoglobulin chain expressed in IgG, IgA, IgM and the like and efficiently measure only the free κ immunoglobulin chain, the free λ immunoglobulin chain, and fragments thereof.

In the step (a) of the test method of the present invention, the subject is not particularly limited. The subject is preferably a human. The subject is, for example, a subject for whom it is necessary to be determined whether or not the subject has developed a psychiatric/neurological disorder. The subject may be a subject determined as having developed a psychiatric/neurological disorder using conventional diagnosis criteria, such as DMSIV-TR, ICD-10, and PANSS. The subject may be a subject not determined as having developed a psychiatric/neurological disorder using conventional diagnosis criteria, such as DMSIV-TR, ICD-10, and PANSS. In addition, the subject may be a subject for whom no information about a psychiatric/neurological disorder is obtained. It may be confirmed in advance whether the subject has a cancer and/or an inflammatory disorder.

In preparing a blood sample, the blood sample is preferably incubated at about 60° C., about 70° C., about 80° C., about 90° C., about 100° C., about 110° C., or about 120° C. for about 1 minute, about 2 minutes, about 3 minutes, about 4 minutes, about 5 minutes, about 6 minutes, about 7 minutes, about 8 minutes, about 9 minutes, or about 10 minutes. Most preferably, it may be incubated at about 100° C. for about 5 minutes.

In the step (b), the normal subject is a subject not having developed or potentially not developing a psychiatric/neurological disorder. For example, the subject is a subject determined as not having developed a psychiatric/neurological disorder using conventional diagnosis criteria, such as DMSIV-TR, ICD-10, and PANSS. The method for the comparison in the step (b) may be a method well-known to those of ordinary skill in the art and is not particularly limited. For example, the measured value obtained in the step (a) can be compared with the measured value of the biomarker for a psychiatric/neurological disorder according to the present invention in a normal subject obtained in advance. Preferably, the results obtained by a two-dimensional electrophoresis method or an enzyme linked immunosorbent assay (ELISA) are compared. When the biomarker for a psychiatric/neurological disorder according to the present invention comprises a plurality of biomarkers, the values measured therefor may be added together for comparison. The measurement of the biomarker for a psychiatric/neurological disorder according to the present invention in a normal subject may be the same as the measurement method described in the step (a).

In most normal subjects, an inflammatory cytokine is below the limit of detection. Thus, the comparison of the amount of the inflammatory cytokine with that from a normal subject may be simply whether or not the inflammatory cytokine is detected. No detection of the inflammatory cytokine can be determined as indicating no change in the cytokine amount as compared with that from a normal subject.

Using the test method of the present invention, whether or not a subject has developed or can potentially develop a psychiatric/neurological disorder can be determined as follows. When the amount of a free κ immunoglobulin chain or a fragment thereof in a blood sample from a subject increases compared to that from a normal subject or is larger than the median value of that from a normal control group, the subject can be determined as having developed or potentially developing a psychiatric/neurological disorder. Alternatively, when the amount of a free λ immunoglobulin chain or a fragment thereof in a blood sample from a subject increases compared to that from a normal subject, the subject can be determined as having developed or potentially developing a psychiatric/neurological disorder. Alternatively, when the amount of a free κ immunoglobulin chain or a fragment thereof and a free λ immunoglobulin chain or a fragment thereof in a blood sample from a subject increases compared to that from a normal subject or is larger than the median value of that from a normal control group, the subject can be determined as having developed or potentially developing a psychiatric/neurological disorder.

Using the test method of the present invention, whether or not a subject has developed or can potentially develop a psychiatric/neurological disorder can also be determined as follows. When the amount of a free κ immunoglobulin chain or a fragment thereof in a blood sample from a subject increases compared to that from a normal subject or is larger than the median value of that from a normal control group, and the amount of an inflammatory cytokine does not change compared to that from a normal subject or is not detected, the subject can be determined as having developed or potentially developing a psychiatric/neurological disorder. Alternatively, when the amount of a free λ immunoglobulin chain or a fragment thereof in a blood sample from a subject increases compared to that from a normal subject or is larger than the median value of that from a normal control group, and the amount of an inflammatory cytokine does not change or is not detected compared to that from a normal subject, the subject can be determined as having developed or potentially developing a psychiatric/neurological disorder. Alternatively, when the amount of a free κ immunoglobulin chain or a fragment thereof and a free λ immunoglobulin chain or a fragment thereof in a blood sample from a subject increases compared to that from a normal subject and the amount of an inflammatory cytokine does not change or is not detected compared to that from a normal subject, the subject can be determined as having developed or potentially developing a psychiatric/neurological disorder.

"Increase" can be increasing about 1.5-fold, about 2-fold, about 3-fold, about 4-fold, about 5-fold, about 10-fold, about 15-fold, about 20-fold, about 30-fold, about 50-fold, about 100-fold, or more. "Not change" refers to that the amount of the biomarker for a psychiatric/neurological disorder according to the present invention is the same or is not significantly different between the amount from a subject in the step (a) and that from a normal subject in the step (b). "Not significantly different" refers to, for example, that the p value is less than 0.05, or the difference is about 0.1%, about 0.2%, about 0.3%, about 0.4%, about 0.5%, about 1%, about 2%, about 3%, about 4%, about 5%, about 10%, about 20%, or about 30%.

"Larger than the median value" means, for example, larger than the median value in the normal control group. The median value in the normal control group may be a known median value as described, for example, in Non-patent Literature 1, or a value calculated from the actual measurement in the normal control group.

EXAMPLES (5. Examples)
Examples of the present invention will be described below. The following Examples are described for a better understanding of the scope of claims of the present invention, and not intended to limit the scope of claims of the present invention.

Example 1

Poly IC (polyriboinosinic-polyribocytidilic acid) (Sigma Co., Ltd.) dissolved in saline was intraperitoneally administered in an amount of 4 mg/kg to a Wistar rat at day 15 of gestation before normal delivery to prepare maternal immune activation model rats (MIA rats) which were schizophrenic and autistic model animals. The MIA rat is one of psychiatric/neurological disorder model animals (see Limin Shi et al, J. Neurosci. 2003 Jan. 1; 23(1): 297-302 and Arata Oh-Nishi et al, Brain Research, Volume 1363, 6 Dec. 2010, Pages 170-179). Only an equal volume of saline was intraperitoneally administered to another Wistar rat at day 15 of gestation before normal delivery to prepare control rats (hereinafter, referred to as "control" rats) as a control group. The MIA rats had significantly attenuated PPI compared to the control rats and were confirmed to be capable of being used as psychiatric/neurological disorder model animals.

The sera of the MIA rats (12-week old) and the control rats (12-week old) were collected and denatured with urea/thiourea, DTT, and SDS, followed by separating protein by a 2-dimensional electrophoresis method. Electrophoresis gel images are shown in FIG. 2. As a result of analyzing the images using an image analysis software (Progenesis PG220; from Shimadzu Corporation), spot 1115 (about 25 kDa) was found to be significantly increased in the MIA rats (described as "Poly IC" in the figure) compared to that in the control rats (described as "Saline" in the figure). The spot was cut out, and the protein was identified by a LC MS/MS measurement method; as a result, it was found to be a κ immunoglobulin chain C region (Ig κ-C) (FIG. 3).

The free κ immunoglobulin chain consists of a constant region (κ immunoglobulin chain C region) of about 12 kDa and a variable region of about 12 kDa. The variable region frequently changes in the amino acid sequence and thus is not detected by a mass spectrometer (MS). The spot in which the significant difference was seen was observed around about 25 kDa and thus it may be actually a free κ immunoglobulin chain.

Example 2

A rat-derived κ immunoglobulin chain C region (SEQ ID NO: 4) was used as an antigen and administered to a rabbit for immunization to prepare an antibody (anti-Ig κ-C antibody). Using the same method as that in Example 1, MIA rats and control rats were prepared. The sera of the MIA rats (12-week old, N=7) and the control rats (12-week old, N=7) were denatured only with SDS (100° C., 5 minutes) and subjected to electrophoresis with SDS-polyacrylamide gel to separate protein. Thereafter, Western blotting was carried out (gel: 10 to 20%, primary antibody (1:1,000), secondary antibody (1:5,000)) (FIG. 4). The anti-Ig κ-C antibody was used as a primary antibody, and an anti-rabbit IgG-HRP (from Chemi-Con Co., Ltd.) was used as a secondary antibody.

The intensity of a band of about 25 kDa significantly increased in the MIA rats ("Poly IC" in FIG. 4) compared to that in the control rats ("Saline" in FIG. 4) (FIG. 4(2)). The band of about 25 kDa is the free κ immunoglobulin chain since it is detected without the cleavage of S-S bonds or hydrogen bonds. These results clearly show that the free κ immunoglobulin chain serves as a biomarker for a psychiatric/neurological disorder.

Example 3

The amounts of inflammatory cytokines in the serum were measured in the MIA rats ("Poly IC" in the table, 12-week old, N=7) and the control rats ("Saline" in the table, 12-week old, N=7) of Example 2. The measurement of the amount of inflammatory cytokines used Quantikine ELASA Rat IL-1β, IL-6, and TNF-α (from R&D Co., Ltd.).

TABLE 1

Concentration of Inflammatory Cytokine in Serum

|  | IL-6 (pg/ml) | IL-1beta (pg/ml) | TNF-alpha (pg/ml) |
|---|---|---|---|
| Saline | N.D | N.D | N.D |
| Poly IC | N.D | N.D | N.D |
|  | (N.D < 250) | (N.D < 96) | (N.D < 25) |

No increase of the inflammatory cytokines in sera was observed in the MIA rats ("Poly IC" in the table) and the control rats ("Saline" in the table).

Example 4

The usefulness of the biomarker for a psychiatric/neurological disorder according to the present invention was tested in a group of schizophrenia patients (SZ) and a group of healthy individuals (Normal).

Serum samples from the SZ and Normal groups, collected according to an IRB-approved protocol, which was given sufficient ethical consideration, were purchased from PrecisionMed Inc. (USA) (acting import agent: Wako Pure Chemical Industries, Ltd.).

The amounts of the free κ immunoglobulin chain and the free λ immunoglobulin chain in the sera were measured using FREELITE κ Chain (MBL Co., Ltd., code number: BS-LK016BD) and FREELITE κ chain (MBL Co., Ltd., code number: BS-LK018BD) according to the instructions of the provider. The inflammatory cytokines were measured using AlphaLASA Human IL-1 beta, IL-6, and TNF-alpha Kits (from PerkinElmer Inc., code numbers: AL223 C/F, AL220 C/F, and AL208 C/F).

Basic data and the data summarizing average values in the group of schizophrenia patients (SZ) and the normal group are shown in Tables 2 and 3 below (psychopathological score: PANSS score).

TABLE 3

Summary of Basic Data

|  | Normal (N = 7) | SZ (N = 11) |
|---|---|---|
| Age | 44.8 ± 4.8 | 43.45 ± 2.79 |
| Age of Onset |  | 22.6 ± 2.7 |
| Positive Symptom |  | 18.6 ± 1.4 |
| Negative Symptom |  | 17.1 ± 1.1 |
| General Psychopathological Score |  | 38.2 ± 2.5 |

Average ± S.E.M

There was no statistically significant difference in age, and the inflammatory cytokines (IL-6, IL-1 beta, and TNF-alpha) were not detected in both of the SZ and normal groups.

FIG. 5 and Table 4 show the results of comparing the concentrations of the free κ immunoglobulin chain (A in FIG. 5) and the free λ immunoglobulin chain (B in FIG. 5) in the sera of the group of schizophrenia patients (SZ) and the normal group. In the schizophrenia patients (SZ), the concentrations of the free κ immunoglobulin chain and the free λ immunoglobulin chain significantly increased (P=0.0012 and P=0.04, respectively). These results clearly show that each the free κ immunoglobulin chain and the free λ immunoglobulin chain individually serves as a biomarker for a psychiatric/neurological disorder. As a result of comparing the concentration of the free κ immunoglobulin chain+the free λ immunoglobulin chain in the group of schizophrenia patients (SZ) and the normal group (C in FIG. 5), a further significant difference was observed (P=0.00063). These results show that it is particularly useful for determining a psychiatric/neurological disorder to combine the free κ immunoglobulin chain and the free λ immunoglobulin chain.

TABLE 2

Basic Data in Schizophrenia Patient(SZ) and Normal Groups

| ID(#) | Race | Age | Age of Onset | Positive Symptom | Negative Symptom | General Psycho pathology | IL6 (pg/ml) | IL-1 beta (pg/ml) | TNF-alpha (pg/ml) |
|---|---|---|---|---|---|---|---|---|---|
| SZ | | | | | | | | | |
| 10226006 | Caucasian | 36 | 21 | 19 | 16 | 34 | ND | ND | ND |
| 10226007 | Caucasian | 35 | 16 | 18 | 16 | 36 | ND | ND | ND |
| 10226029 | Caucasian | 36 | 16 | 17 | 22 | 45 | ND | ND | ND |
| 10226046 | Caucasian | 51 | 20 | 20 | 19 | 41 | ND | ND | ND |
| 10226066 | Caucasian | 61 | 26 | 8 | 15 | 25 | ND | ND | ND |
| 10226067 | Caucasian | 41 | 27 | 24 | 20 | 44 | ND | ND | ND |
| 10226016 | Caucasian | 45 | 45 | 26 | 24 | 53 | ND | ND | ND |
| 10226047 | Caucasian | 58 | 23 | 17 | 14 | 33 | ND | ND | ND |
| 10226063 | Caucasian | 41 | 20 | 23 | 12 | 44 | ND | ND | ND |
| 10226084 | Caucasian | 36 | 17 | 15 | 12 | 27 | ND | ND | ND |
| 10226089 | Caucasian | 38 | 18 | 18 | 19 | 39 | ND | ND | ND |
| Normal | | | | | | | | | |
| 7516 | Caucasian | 25 | — | — | — | — | ND | ND | ND |
| 7520 | Caucasian | 55 | — | — | — | — | ND | ND | ND |
| 7538 | Caucasian | 44 | — | — | — | — | ND | ND | ND |
| 7543 | Caucasian | 62 | — | — | — | — | ND | ND | ND |
| 7551 | Caucasian | 49 | — | — | — | — | ND | ND | ND |
| 7522 | Hispanic | 39 | — | — | — | — | ND | ND | ND |
| 7552 | Hispanic | 40 | — | — | — | — | ND | ND | ND |
|  |  |  |  |  |  |  | (ND < 10) | (ND < 3) | (ND < 10) |

TABLE 4

Concentration of Free Igκ and λ in Serum of Schizophrenia Patient

|  | Normal | SZ |
|---|---|---|
| Free Igκ (mg/l) | 7.89 ± 0.46 (N = 6) | 14.09 ± 1.41** (N = 11) |
| Free Igλ (mg/l) | 10.89 ± 0.94 (N = 7) | 14.04 ± 0.99* (N = 11) |
| Free Igκ + Free Igλ (mg/l) | 17.79 ± 1.16 (N = 6) | 28.14 ± 2.07*** (N = 11) |

(Average ± S.E.M)

In addition, the concentration of free Ig κ in the sera from the 11 patients of the SZ group had higher values (minimum: 9.11 mg/l, maximum: 23.8 mg/l) compared with the median value (7.5 mg/l) of the concentration of free Igh in the sera from healthy individuals aged 40 to 49 years described in Non-patent Literature 1. On the other hand, the median value of the concentration of free Ig λ in the sera from the healthy individuals aged 40 to 49 years is 12.8 mg/l, and 8 of 11 patients in the SZ group had a higher value than the median value (minimum: 9.05 mg/l, maximum: 20.8 mg/l).

INDUSTRIAL APPLICABILITY

The biomarker of the present invention in a blood sample can be measured to perform the primary screening of a psychiatric/neurological disorder in a medical checkup and the like. The screening of a psychiatric/neurological disorder can also be carried out in the first contact of patients in psychiatry.

The invention claimed is:

1. A kit for diagnosing schizophrenia or autism in a subject, comprising:
   (i) a first substance which binds to a biomarker for schizophrenia or autism and thereby detects the biomarker, wherein the substance is labeled and wherein the biomarker is a free κ immunoglobulin chain; and
   (ii) a second substance which binds to a biomarker for schizophrenia or autism and thereby detects the biomarker, wherein the substance is labeled, wherein the biomarker is an inflammatory cytokine and wherein the inflammatory cytokine is at least one member selected from the group consisting of interleukin-6 (IL-6), interleukin-1 beta (IL-1 beta), and tumor necrosis factor-alpha (TNF-alpha).

2. The kit of claim 1, wherein the first substance which binds to the biomarker for schizophrenia or autism is a labeled antibody.

3. The kit of claim 1, wherein the first substance which binds to the biomarker for schizophrenia or autism is immobilized on a solid-phase support.

4. The kit of claim 2, wherein the labeled antibody is a labeled antibody which binds to the amino acid sequence of SEQ ID NO: 5.

5. The kit of claim 1, wherein the free κ immunoglobulin chain comprises the amino acid sequence of SEQ ID NO: 2 or 3.

6. The kit of claim 1, wherein the free κ immunoglobulin chain comprises the amino acid sequence of SEQ ID NO: 1.

7. A kit for diagnosing schizophrenia or autism in a subject, comprising:
(i) a first substance which binds to a biomarker for schizophrenia or autism and thereby detects the biomarker, wherein the substance is labeled and wherein the biomarker is a free λ immunoglobulin chain; and
(ii) a second substance which binds to a biomarker for schizophrenia or autism and thereby detects the biomarker, wherein the substance is labeled, wherein the biomarker is an inflammatory cytokine and wherein the inflammatory cytokine is at least one member selected from the group consisting of interleukin-6 (IL-6), interleukin-1 beta (IL-1 beta), and tumor necrosis factor-alpha (TNF-alpha).

8. The kit of claim 7, wherein the first substance which binds to the biomarker for schizophrenia or autism is a labeled antibody.

9. The kit of claim 7, wherein the first substance which binds to the biomarker for schizophrenia or autism is immobilized on a solid-phase support.

10. The kit of claim 7, wherein the free λ immunoglobulin chain comprises the amino acid sequence of SEQ ID NO: 6.

* * * * *

SEQUENCE LISTING

<160> NUMBER OF SEQ ID NOS: 6

<210> SEQ ID NO 1
<211> LENGTH: 106
<212> TYPE: PRT
<213> ORGANISM: Homo sapiens

<400> SEQUENCE: 1

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 2
<211> LENGTH: 20
<212> TYPE: PRT
<213> ORGANISM: Homo sapiens

<400> SEQUENCE: 2

Ser Val Thr Glu Gln Asp Ser Lys Asp Ser Thr Tyr Ser Leu Ser Ser
1               5                   10                  15

Thr Leu Thr Leu
            20

<210> SEQ ID NO 3
<211> LENGTH: 21
<212> TYPE: PRT
<213> ORGANISM: Homo sapiens

<400> SEQUENCE: 3

Cys Glu Val Thr His Gln Gly Leu Ser Ser Pro Val Thr Lys Ser Phe
1               5                   10                  15

Asn Arg Gly Glu Cys
            20

```
<210> SEQ ID NO 4
<211> LENGTH: 106
<212> TYPE: PRT
<213> ORGANISM: Rattus norvegicus

<400> SEQUENCE: 4

Ala Asp Ala Ala Pro Thr Val Ser Ile Phe Pro Pro Ser Met Glu Gln
1               5                   10                  15

Leu Thr Ser Gly Gly Ala Thr Val Val Cys Phe Val Asn Asn Phe Tyr
            20                  25                  30

Pro Arg Asp Ile Ser Val Lys Trp Lys Ile Asp Gly Ser Glu Gln Arg
        35                  40                  45

Asp Gly Val Leu Asp Ser Val Thr Asp Gln Asp Ser Lys Asp Ser Thr
    50                  55                  60

Tyr Ser Met Ser Ser Thr Leu Ser Leu Thr Lys Val Glu Tyr Glu Arg
65                  70                  75                  80

His Asn Leu Tyr Thr Cys Glu Val Val His Lys Thr Ser Ser Ser Pro
                85                  90                  95

Val Val Lys Ser Phe Asn Arg Asn Glu Cys
            100                 105

<210> SEQ ID NO 5
<211> LENGTH: 20
<212> TYPE: PRT
<213> ORGANISM: Rattus norvegicus

<400> SEQUENCE: 5

Ser Val Thr Asp Gln Asp Ser Lys Asp Ser Tyr Ser Met Ser Ser
1               5                   10                  15

Thr Leu Ser Leu
            20

<210> SEQ ID NO 6
<211> LENGTH: 94
<212> TYPE: PRT
<213> ORGANISM: Homo sapiens

<400> SEQUENCE: 6

Ala Pro Ser Val Thr Leu Phe Pro Pro Ser Ser Glu Glu Leu Gln Ala
1               5                   10                  15

Asn Lys Ala Thr Leu Val Cys Leu Ile Ser Asp Phe Tyr Pro Gly Ala
            20                  25                  30

Val Thr Val Ala Trp Lys Ala Asp Ser Ser Pro Val Lys Ala Gly Val
        35                  40                  45

Glu Thr Thr Thr Pro Ser Lys Gln Ser Asn Asn Lys Tyr Ala Ala Ser
    50                  55                  60

Ser Tyr Leu Ser Leu Thr Pro Glu Gln Trp Lys Ser His Lys Ser Tyr
65                  70                  75                  80

Ser Cys Gln Val Thr His Glu Gly Ser Thr Val Glu Lys Thr
                85                  90
```